United States Patent [19]

Gross et al.

[11] 4,008,254
[45] Feb. 15, 1977

[54] CERIA CATALYZED CONVERSION OF PHENOLS TO DIBENZOFURANS IN THE PRESENCE OF WATER VAPOR

[75] Inventors: David E. Gross, St. Charles; Norman A. Fishel, Olivette, both of Mo.

[73] Assignee: Monsanto Company, St. Louis, Mo.

[22] Filed: Aug. 8, 1975

[21] Appl. No.: 603,063

[52] U.S. Cl. .................................. 260/346.2 M
[51] Int. Cl.² .................................. C07D 307/91
[58] Field of Search .................... 260/346.2 M

[56] References Cited

UNITED STATES PATENTS

| | | | |
|---|---|---|---|
| 1,808,349 | 6/1931 | Hale et al. | 260/346.2 M |
| 2,620,357 | 12/1952 | Arundale et al. | 260/596 |
| 3,108,121 | 12/1963 | Walsh et al. | 260/346.2 |

FOREIGN PATENTS OR APPLICATIONS

| | | | |
|---|---|---|---|
| 168,291 | 10/1904 | Germany | |
| 929,376 | 6/1963 | United Kingdom | 260/346.2 M |

OTHER PUBLICATIONS

Pope, Chem. Week. 61, 598–600, (1965).
Graebe et al., Ber., 29, 1877 (1896).
Tauber et al., Ber. 25, 2745 (1892).
Cullinane, J. Chem. Soc., 2267 (1930).
Shiotani et al., Angew Chem. 86, 478 (1974).
Sabatier et al., (I), *Compt. Rend.* 151, pp. 492–494, (1910).
Tolstopyatova, *Chem. Abst.* vol. 65, 18376c (1966).
Sabatier et al., (II), Compt. Rend. 155, pp. 260–262 (1913).
Kirk–Othmer, *Encyclopedia of Chem. Technology*, Sec. ed., John–Wiley Publ. Co., vol. 20, p. 248, (1969), and vol. 4, p. 852, (1964).

*Primary Examiner*—Henry R. Jiles
*Assistant Examiner*—ernard Dentz
*Attorney, Agent, or Firm*—Joseph D. Kennedy; John D. Upham

[57] ABSTRACT

A method for preparation of heterocyclic fused ring compounds by dehydration and dehydrogenation of certain phenolic compounds in the presence of water vapor and in the presence of a cerium oxide catalyst is disclosed. Preferred phenolic compounds, catalytic materials, and reaction conditions also are described.

15 Claims, No Drawings

CERIA CATALYZED CONVERSION OF PHENOLS TO DIBENZOFURANS IN THE PRESENCE OF WATER VAPOR

BACKGROUND OF THE INVENTION

1. Field of the Invention

The present invention relates to a novel catalytic method for preparation of fused ring heterocyclic compounds. More particularly this invention relates to a process for catalytic dehydration and dehydrogenation of certain phenolic compounds having a hydrogen atom in at least one of the positions ortho to the hydroxyl group, to prepare certain fused ring heterocyclic compounds wherein the heterocyclic ring is a five-membered ring oxide.

2. Prior Art

Fused ring heterocyclic compounds such as dibenzofuran, substituted dibenzofurans, and similar compounds including five-membered ring oxides are useful materials. For example, dibenzofuran, also known as diphenylene oxide, and derivatives thereof are useful intermediates for preparation of dyestuffs, stabilizers for organic materials, and other useful chemicals. In addition, dibenzofuran is useful as a functional fluid, as a high boiling solvent for various organic materials, and as has been shown by Pope in Chem. Weekbl., 61, 598–600(1965), the eutectic mixture of dibenzofuran and biphenyl may be used as a heat transfer agent.

Commercial use of these materials has been hampered however, by reason of high costs, presence of impurities, and general unavailability. Commercially available dibenzofuran for example is presently obtained from coal tar and frequently contains impurities such as acenaphthene and fluorene which cannot conveniently be separated by commercially suitable methods such as washing, recrystallization, or distillation. In some cases dibenzofuran having greater purity as compared to that obtained from coal tar may be synthesized, but the prior art methods are costly because of expensive starting materials, complicated procedures, low yields or the like. For example, dibenzofuran has been obtained in a 30% yield by Graebe and Ullmann [Ber. 29, 1877 (1896)] by diazotization and subsequent hydrolysis of 2'-aminodiphenyl oxide, while Tauber and Halberstadt [Ber., 25, 2745 (1892)] obtained a yield of 75% by similar treatment of 2,2-diaminodiphenyl. These two methods however are not adapted to commercial operation due to the high cost and difficulty of obtaining the starting materials required. Hale and Stoesser (U.S. Pat. No. 1,808,349) obtained dibenzofuran by intramolecular dehydrogenation of orthophenylphenol over a refractory oxide catalyst, but again the high cost of the starting material limits the commercial utility of this route. Cullinane [J. Chem. Soc., 2267 (1930)] obtained dibenzofuran in 20% yield in eight hours by pyrolysis of phenol over litharge at 150° C. The low yield limits commercial utility of this route. Walsh and Preston (U.S. Pat. No. 3,108,121) reacted diphenyl oxide over a relatively expensive and sensitive 5% platinum on charcoal catalyst to obtain dibenzofuran. Shiotani and Itatani [Angew.Chem. 86 478 (1974)] used as palladium acetate catalysts to produce dibenzofuran from diphenyl oxide but obtained much dimerized product as well. In particular, in these latter two methods two synthetic steps are required to obtain dibenzofuran from phenol inasmuch as diphenyl oxide is frequently obtained from a reaction involving a condensation of phenol.

In summary, the art is replete with teachings showing the synthesis of dibenzofuran, none of which however is believed to be attractive for commercial production of dibenzofuran and substituted dibenzofurans.

SUMMARY OF THE INVENTION

It has now been discovered that dibenzofuran and substituted dibenzofurans for example, 2,8-dimethyldibenzofuran or 4-phenyldibenzofuran, can be produced economically in high yield by a simple and highly selective process wherein phenol and certain substituted phenols generally designated as phenolic compounds more specifically described hereinafter are subjected to dehydration and dehydrogenation at elevated temperatures in the presence of water vapor and in the presence of a catalyst comprising cerium oxide. These results are surprising because there was no reason to believe that the apparently substantially simultaneous dehydration and dehydrogenation would occur in the presence of water vapor in the presence of a catalyst comprised of cerium oxide especially in view of the work of Arundale and Mottern (U.S. Pat. No. 2,620,357) which required mixtures of cerium oxide with the oxides of zinc, magnesium or beryllium to be effective for dehydration and dehydrogenation of glycol compounds.

Accordingly, it is an important object of the present invention to provide a selective process for production of dibenzofuran and substituted dibenzofurans in high yield.

Another object is to provide a process for production of dibenzofuran and substituted dibenzofurans wherein phenol or certain substituted phenols are subjected to dehydration and dehydrogenation at elevated temperatures in the presence of water vapor and in the presence of a cerium oxide catalyst.

Still another important object is to provide a process for production of dibenzofuran and substituted dibenzofurans which is commercially economical and which may be conducted in a batch or continuous manner.

Yet another object is to provide a process for production of dibenzofuran and substituted dibenzofurans which may be effected under subatmospheric, atmospheric, or superatmospheric conditions.

Another important object is to provide a process for production of dibenzofuran and substituted dibenzofurans wherein the presence of water vapor when added to the feedstocks decreases the rate of loss of activity of the catalyst during the dehydration dehydrogenation reaction.

These and other objects and advantages of the present invention will become apparent in view of the following detailed description which covers several preferred embodiments thereof.

DESCRIPTION OF THE PREFERRED EMBODIMENTS

The objects of the present invention are accomplished by a process of forming dibenzofuran and substituted dibenzofurans at elevated temperatures with a catalyst preferably comprised of cerium oxide. Under the influence of the catalyst both a dehydration and a dehydrogenation reaction take place in a manner such that one molecule of water is released and an ether linkage formed between two molecules of reactants and one hydrogen molecule is released, one hydrogen atom being removed from one ortho position of each phenyl compound, and a second link is formed between the two constituents at the aforesaid ortho positions to produce a five-membered ring oxide. It will, therefore, be understood that phenol, derivatives of phenol, and other phenolic compounds may be used in the process of the present invention provided that they include an unsubstituted ortho position, that is having a hydrogen atom present, relative to the hydroxyl group on each aromatic nucleus.

It should be understood that the phenolic reactants used for the process of this invention may be either unsubstituted, that is phenol, or substituted in one or more positions on either side of the hydroxyl group that is in the 2, 3, 4, 5 or 6 positions, or on any side chain associated with the aromatic nucleus so long as there is a hydrogen atom in at least one of the positions which is ortho to the hydroxyl group. Thus as it will be readily appreciated, the phenolic reactants may be substituted in many different ways with a wide variety of substituents, subject to the usual reservation that the said substituents are non-interfering substituents. That is to say, the phenolic reactants should not have substituents which would substantially interfere with the present dehydration and dehydrogenation process as, for instance, by poisoning the catalyst.

Thus, unless otherwise indicated herein, phenols and like expressions such as phenolic compounds are employed in the generic sense and are intended to include phenol or phenol substituted in the manner previously described such that there is a hydrogen atom in at least one of the positions ortho to the hydroxyl group but may also have additional substituents on the carbon atoms of the benzene ring or on any side chain associated therewith. Thus the generic term phenols may be taken to include phenol itself, alkyl substituted phenols, hydroxy substituted phenols, aryl substituted phenols, aralkyl substituted phenols, alkaryl substituted phenols, polycyclic phenols and the like. Suitable alkyl substituted phenols include all phenolic materials which otherwise satisfy the condition of an unsubstituted ortho position, however, it is preferred to use alkyl substituted phenols wherein the alkyl group contains between one and six carbon atoms, more preferably between one and three carbon atoms such as ortho, meta, and paracresol; ortho, meta, and para ethylphenol; 2,5-xylenol, 2,4-xylenol and 3,4-xylenol. When the alkyl group contains more than two carbon atoms, it may be straight or branched chain as, for example, the alkyl group may be either n-propyl or isopropyl. In a similar manner, suitable hydroxy substituted phenols include all phenolic compounds otherwise satisfying the above-mentioned requirements, including phenols substituted with several hydroxy groups such as pyrocatechol, resorcinol, or pyrogallol. Aryl substituted phenols include phenyl substituted phenols in general although it is preferred to use materials such as ortho, meta, and para phenylphenol, more preferably orthophenylphenol. Aralkyl substituted phenols include materials wherein the aromatic portion of the aralkyl group is phenyl or the like and the alkylene portion of the group contains between one and six carbon atoms, straight or branched chain, more preferably between one and three carbon atoms such as ortho, meta, and para benzylphenol. Alkaryl substituted phenols include phenolic compounds wherein the aromatic portion of the alkaryl group is phenylene or the like and the alkyl portion of the group preferably contains between one and six carbon atoms, straight or branched chain, more preferably between one and three carbon atoms such as the methyl phenylphenols. Finally suitable polycyclic phenols include such materials as 1-naphthol and 2-naphthol.

Inasmuch as the instant process is preferably carried out in the vapor phase in the presence of water vapor, the phenolic starting material should preferably be a vaporizable material. That is, the reactant should have sufficient thermal stability for vaporization without decomposition at atmospheric pressure and its boiling point should be below the selected dehydration and dehydrogenation temperature, for example below about 600° C in most instances. The phenols should also be stable in the presence of water vapor at the conditions selected for the dehydration and dehydrogenation reactions. The aforesaid phenols typically have such characteristics.

In accordance with the present process, the aforesaid phenolic reactants may be converted by the dehydration and dehydrogenation reactions of the hydroxyl groups and ortho hydrogen atoms into the corresponding compounds having a five-membered ring oxide, that is a fused ring system containing a carbocyclic ring having unsaturation of the benzene type fused directly to a heterocyclic furan ring with the furan ring in turn fused to a second carbocyclic ring having unsaturation of the benzene type, with the proviso that said fused ring system may further have any substituents corresponding to the substituents on the phenolic reactants. It should be understood that dibenzofurans as employed herein unless indicated otherwise, like phenols, is employed in the generic sense to mean dibenzofuran, substituted dibenzofurans and other similar compounds as described above.

By way of a non-limiting example, some of the many products which may be synthesized by the instant process may be represented by the formula:

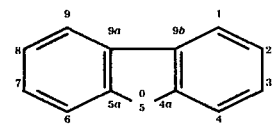

wherein certain of the positions, numbered herein according to the convention used presently by Chemical Abstracts, may independently be substituents of the type discussed in connection with the phenolic compounds suitable as reactants. For example, dibenzofuran, 2,8-dimethyldibenzofuran, 4,6-dimethyldibenzofuran, 3,7-dimethyldibenzofuran, 1,7-dimethyldibenzofuran, 4,6-dihydroxydibenzofuran, 1,7-dihydroxydibenzofuran, 3,7-dihydroxydibenzofuran, 4,6-diphenyldibenzofuran, 2,8-diphenyldibenzofuran, as well as others named herein.

A catalyst is essential in the practice of this invention, and as such, must be a material capable of catalyzing the dehydration and dehydrogenation of phenolic compounds of the type described herein. Cerium oxide, for example, has been found useful as a catalytic material and may be used in combination with other materials which are sufficiently refractory to withstand the elevated reaction temperature at which the reaction is preferably conducted. For example, oxides of aluminum, silicon, magnesium, titanium, zirconium, hafnium, calcium, potassium, sodium, lanthanum, neodymium, praseodymium, samarium, thorium, and uranium as well as mixtures thereof may be used in combination with cerium oxide as the active catalytic material. The extent of desired reactions obtained by using less than 1% by weight of the cerium oxide is perceptible but not sufficient to be of any appreciable value. Cerium oxide which is essentially pure may be used as the active catalytic material. If desired the catalyst may be charged to the reactor as an oxide or converted to the oxide in situ prior to the dehydration and dehydrogenation reactions. In accordance with various practices of the art, the active catalyst may be used unsupported, or dispersed or supported on a suitable carrier material, such as alumina or silica alumina (e.g. 50–95% silica), supported or unsupported, in the reaction mixture which may include a solvent such as benzene, biphenyl, toluene or the like.

For the dehydration and dehydrogenation reactions, the phenolic reactants along with water or water vapor are introduced into the reaction vessel containing the catalyst which is maintained at a temperature high enough to vaporize the reactants and also high enough to induce a good reaction rate so that an adequate yield of the product may be obtained at reasonable space velocities as hereinafter described. On the other hand, it is preferred that the temperature should not be raised so high that the yield drops off or decomposition of the products or starting materials occurs. In general the reaction temperature is desirably above about 300° C or preferably from about 300° to 700° C. The preferred temperature range, however, will depend somewhat on the starting materials and the products in relationship to their susceptibility to decomposition and like factors as discussed above. In particular for phenol the reaction temperature is preferably above about 350° C with optimum results being obtained within the range of about 450° to 600° C. For paracresol the reaction temperature is preferably above about 475° C with optimum results being obtained within the range of about 500° to 600° C. The temperature of the reaction chamber may be controlled in conventional manner such as by an electrically heated jacket, to maintain the desired operating temperature.

Reaction pressure is not particularly critical, so subatmospheric, atmospheric, or superatmospheric pressures may be used according to desire. However, it is seldom desirable to raise the reaction pressure such that the process is converted into either a mixed phase or liquid phase reaction as opposed to the preferred vapor phase reaction. It is nonetheless contemplated within the scope of this invention that superatmospheric pressures up to about 150 atmospheres or higher may be employed. In the event that superatmospheric pressures are employed, the pressures may be provided by introducing into the reaction zone in addition to water vapor, a gas such as nitrogen or hydrogen, the amount of pressure which is employed being that which is sufficient to maintain a major portion of the reactants in the liquid phase while a minor portion are in the vapor phase, however, higher pressures may be used. On the other hand, the amount of gas which is employed may be limited to that which is sufficient to produce the desired superatmospheric pressure, however, the amount being less than that which produces condensation of the reactants. In general, atmospheric pressure is preferred for convenience, simplicity, and economy in carrying out the reaction.

The process of this invention may be effected in any suitable manner and, for example, may comprise either a batch or continuous type operation. When a batch type operation is used, a quantity of the starting material suitable for the capacity of the reaction vessel employed is placed in an appropriate apparatus along with the catalyst. The particular reaction apparatus may comprise a glass or metal flask or its commercial counterpart, in the event that the reaction is to be effected at near atmospheric pressure. Conversely, when the reaction is to be conducted at subatmospheric or superatmospheric pressure, the reaction apparatus should be a pressure resistant vessel, for example, an autoclave of the rocking, rotating, or mixing type. In the event that the latter system is employed, and the reaction is conducted at superatmospheric pressure, the autoclave is sealed and gas such as hydrogen or nitrogen may be pressed in until a superatmospheric pressure within the range hereinbefore set forth has been reached. Following this the autoclave and contents thereof are heated to the desired operating temperature which is above 300° C and maintained thereat for a predetermined period of time which may range from about 0.5 hours up to 10 hours or more in duration. While the period of time necessary to conduct the reaction depends upon parameters such as the activity of the catalyst, the reaction temperature, the reaction pressure, and the like, it must be an effective period of time, which may of course be limited in duration if the starting materials or products tend to decompose under the reaction conditions. At the end of the reaction period, the autoclave contents are allowed to return to room temperature, the excess pressure discharged, and the reaction mixture recovered. If the reaction vessel is a flask, the reaction mixture is treated in a similar manner, that is, by allowing the flask contents to return to room temperature after the reaction period, followed by recovery of the reaction mixture. The reaction product may be separated from the catalyst by conventional means such as filtration.

It is also contemplated within the scope of this invention that the process described herein may be effected in a continuous manner. One particular method comprises a fixed bed operation in which the reactant feed stream is continuously charged to a reactor containing a fixed bed of catalyst, the reactor being maintained, at the desired operating temperature, broadly 300° to 700° C, preferably about 400° to 600° C, thereby allowing the heated reactants to contact the heated catalyst. Other means of accomplishing a continuous operation are by using the catalyst in a moving bed system or a fluidized bed system; however, in view of the well known operational advantages, it is preferred to use a fixed bed system. The reactor may be operated at subatmospheric, atmospheric, or superatmospheric pressure e.g. from 0.1 to 100 atmospheres, absolute. It is also contemplated that within the scope of the invention that in addition to water vapor, gases such as nitrogen and hydrogen as well as mixtures thereof may be continuously or intermittently charged to the reaction zone so long as the gases and reactants are preheated by any suitable means to the desired reaction temperature prior to introduction to the reaction zone. In general the proportion of water vapor is from 0.01 to equal proportions by weight relative to the phenolic feedstock, and the proportion of nitrogen or hydrogen is from 0.5 to 12 moles of the nitrogen or hydrogen per mole of the phenolic feedstock. The reactants may be passed over the catalyst bed in either upward or downward flow for example, and the products withdrawn continuously, allowed to cool, and recovered. In the event it is desired to operate the reactor at subatmospheric or superatmospheric pressure conventional means for obtaining such condition, for example by use of mechanical vacuum pumps or mechanical compressors may be employed.

The space velocity of the reactants through the active catalyst zone may vary considerably depending upon for example, the reactivity of the starting material, the activity of the catalyst, and the reaction temperature. In addition, the reaction mixture may be recycled separately over a single catalyst mass or sequentially passed over several catalysts of the same or different composition. However, high yields per pass are obtainable in the case of phenol itself and it is usually preferred to recycle only the unreacted material in the product stream after the product has been separated therefrom. The gas hourly space velocity (GHSV) is preferably selected from the range of about 1 $hr^{-1}$ to 2000 $hr^{-1}$, however lower space velocities may be employed.

After a period of operation when the catalyst may become deactivated by the presence of carbonaceous deposits, the catalyst may be reactivated or regenerated by passing an oxygen containing gas, for example air, air mixed with nitrogen, or air mixed with steam, into contact with the catalyst at an elevated temperature in order to burn carbonaceous deposits from the catalyst e.g. temperatures of 300° C to 1000° C may be employed. The method of regenerating the catalyst will depend on whether there is a fixed bed, moving bed, or fluidized bed operation. Regeneration methods and conditions are well known in the art.

The following examples are given to illustrate the process of the present invention, and are not intended to limit the generally broad scope of the present invention.

EXAMPLE 1

In this example, 8164 grams of cerium nitrate, 99.9% by weight cerium with respect to other lanthanides, is charged to a muffle furnace maintained at about 450° C and removed after a roasting period of about 5 hours. The 3242 grams of cerium oxide recovered is pressed through a 50 mesh screen. The resulting material is a finely divided powder and is designated catalyst A.

EXAMPLE 2

In this example, to 200 grams of catalyst A is added 2 grams of Acheson grade No. 38 graphite powder and the resulting material is thoroughly mixed by tumbling. The mixture is then pressed by conventional techniques into right-cylindrical tablets of approximately 3.2 mm in length and 3.2 mm in diameter. The graphite is essentially used as a lubricant in the pressing operation. The 194 grams of tablets obtained are placed in a muffle furnace maintained at about 600° C and are removed after a period of about four hours. The tablets which are recovered weigh 188 grams and are designated catalyst B.

EXAMPLE 3

In this example, 269 grams of $Ce(NO_3)_3 \cdot 6H_2O$ are dissolved in 1 liter of deionized water and the resulting solution is filtered through No. 1 filter paper. To 1 liter of deionized water are added 113g of 30 weight percent hydrogen peroxide solution and a sufficient amount of 58 weight percent $NH_4OH$ solution to adjust the resulting solution to about pH 9. To this second solution are alternately added portions of the cerium nitrate solution and a sufficient amount of additional 58 weight percent $NH_4OH$ solution to maintain the pH at about 9. After combination is complete, the mixture is stirred at ambient temperature for about 15 minutes, then while continuing to stir, the mixture is heated to about 95° C for a period of 1 hour. The mixture is allowed to cool to ambient temperature, allowed to settle, and then filtered through No. 1 filter paper. The bright yellow filter cake is then washed twice with 200 ml portions of deionized water and filtered again. A 202.9 gram portion of the washed filter cake is then extruded in conventional manner through a die about 1.6 mm diameter. The extrudate is then oven-dried overnight at about 120° C to yield a net 162.9 grams of dried material which is then placed in a muffle furnace which is maintained at about 600° C for a period of about 4 hours. The resulting catalyst is designated catalyst C.

EXAMPLE 4

In this example, 28.52 grams of a support which is essentially alpha alumina in the form of about a 3.2 mm diameter by 3.2 mm long extrudate is dried in a muffle furnace maintained at 300° C for a period of about 5 hours. The surface area of the support material as measured by nitrogen absorption is about 0.03 square meters per gram. To 50 grams of deionized water is added 100g of $Ce(NO_3)_3 \cdot 6H_2O$ which is stirred until dissolution of the solid cerium nitrate hydrate occurs. The support is contacted with the solution for a period of 5 minutes, the excess solution allowed to drain by dripping, and then overnight placed in a forced air oven maintained at 120° C. The composite material is then placed in a muffle furnace which is then heated to 600° C and maintained thereat for a period of 4 hours. The recovered material weighs 32.47 grams and contains 12.2% by weight of cerium oxide and is designated catalyst D.

EXAMPLE 5

In this example, 4117 grams of cerium hydrate which is comprised of about 92% by weight cerium and 8% by weight neodymium and praseodymium as hydrates, is mixed by thorough tumbling with 83 grams of Acheson grade No. 38 graphite. The mixture is then pressed by conventional techniques into right-cylindrical tablets of approximately 4.8 mm diameter and 4.8 mm in length. The 3614 grams of tablets obtained are placed in a muffle furnace maintained at about 600° C and are removed after a period of about four hours. The tablets which are recovered weigh 3036 grams and are designated catalyst E.

EXAMPLE 6

In this example, 15 grams of catalyst A are thoroughly mixed by tumbling with 0.6 grams of Acheson grade No. 38 graphite and 15 grams of gamma alumina trihydrate precursor and the resulting mixture pressed by conventional means into right-cylindrical tablets of about 3.2 mm diameter and 3.2 mm in length, to yield 24.3 grams of tablets. The tablets are dried for about 3 hours in a muffle furnace maintained at 300° C and are then calcined for a period of 6 hours at 600° C. The 21.5 grams of tablets recovered are designated catalyst F.

EXAMPLE 7

In this example, 505 grams of cerium nitrate hydrate is dissolved in sufficient deionized water to produce 1740 ml of solution. A second solution is prepared by dissolving 313g of oxalic acid in 300 ml of deionized water which is heated to about 80° C. The cerium nitrate solution is added slowly with stirring to the oxalic acid solution over a period of about 90 minutes. The mixture is maintained at about 80° C during the addition period and for about an additional 60 minutes. The mixture is allowed to cool and is filtered. The cerium oxalate hydrate filter cake is slurried in one liter of deionized water and again filtered. A second and third slurrying and filtration are conducted in a similar manner except 1.5 liters of deionized water are used each time. The wet filter cake is then dried overnight in a forced air oven maintained at 100° C. The recovered oxalate weighs 353 grams. A 100 gram portion of this oxalate is placed in a muffle furnace and is calcined for 2 hours at 150° C, about 1 hour heat up to 450° C, and 5 hours at 450° C. The recovered cerium oxide weighs 59g to which is added 0.6 grams of Acheson grade No. 38 graphite powder. The cerium oxide and graphite are then thoroughly mixed by tumbling and then pressed by conventional means into right-cylindrical tablets approximately 3.2 mm in diameter and 3.2 mm long. The 49.1 grams of tablets obtained in this manner are placed in a muffle furnace and are then roasted at about 300° C for a period of 1 hour and then at 600° C for about 5 hours. The recovered tablets weigh 46.7 grams and are designated catalyst G.

EXAMPLE 8

In this example, 41.1 grams of catalyst F are contacted with a solution formed by addition of 1.2 grams of $Ca(NO_3)_2 \cdot 4H_2O$ to eight ml of deionized water. The mixture is stirred and the excess water allowed to evaporate and is then dried in a forced air oven at 120° C for a period of 5 hours. The mixture is then charged to a muffle furnace, dried at 300° C for about 2 hours and then roasted at 700° C for about 5 hours. The resulting material is designated catalyst H.

EXAMPLE 9

In this example, pellets of catalyst B are crushed to a particle size range of 10 to 16 mesh and introduced into a heat resistant glass tube reactor equipped with an axial thermocouple well to form a fixed bed with a volume of 15 cc supported on a plug of glass wool. A layer of crushed quartz chips is placed on top of the catalyst bed to form a preheating zone for the catalyst.

The catalyst bed is heated to 500° C and held there throughout the reaction while the liquid feed which is composed of nine parts by weight phenol and one part by weight water is charged through a capillary to the top of the reactor at a rate equivalent to a GHSV of 80 $hr^{-1}$. Atmospheric pressure is employed for the reaction.

A product stream is taken off the bottom of the reactor, allowed to cool to room temperature to condense the normally liquid contents. By vapor phase chromatographic analysis the liquid condensate is found to contain 43.4 percent by weight of dibenzofuran when corrected for the water introduced in the feed.

EXAMPLE 10

In this example, 18.9 grams of catalyst C are introduced into a heat resistant glass tube reactor equipped with an axial thermocouple well to form a fixed bed with a volume of 10 cc supported on a glass wool plug. A layer of crushed quartz chip is placed on top of the catalyst bed to form a preheating zone for the catalyst.

The catalyst bed is heated to 550° C and held there throughout the reaction while the liquid feed comprised of 89.5 percent by weight phenol and 10.5 percent by weight water is charged through a capillary to the top of the reactor where it is mixed with a hydrogen stream in the ratio of four moles of hydrogen per mole of phenol. The total feed rate is equivalent to a GHSV of 450 $hr^{-1}$. After 3.5 hours of reaction time the product stream is found to contain 27.8 percent by weight dibenzofuran when corrected for the water introduced in the feed.

When this example is repeated except using a feed which contains essentially no water, the product stream is found to contain 15.0 percent by weight dibenzofuran after 3.5 hours of reaction time.

EXAMPLE 11

In this example 2040 grams of catalyst E are placed in a stainless steel reactor fitted with an axial thermowell and electrical heaters. A feed comprised of 20 percent by weight water and 80% by weight phenol is charged to a vaporizer at a phenol rate equivalent to 46 $hr^{-1}$ GHSV. The vaporizer exit is connected to the reactor inlet. The catalyst is maintained at about 532° C. After a period of 18 hours after starting the feed, the product is analyzed and found to contain 33.6 percent by weight dibenzofuran when corrected for the water in the feed.

It should be apparent, however, that the particular embodiments chosen to illustrate the invention are not all inclusive and that many changes and variations could be made therein, some of which for example depend upon the activity of the particular catalyst and upon the nature of the starting material. All such changes, modifications, variations or the like, however, which will be apparent to those skilled in the art after considering this disclosure and which do not depart from the spirit and scope of this invention are deemed to be covered by the subjoined claims.

What is claimed is:

1. Process for the production of a dibenzofuran compound which comprises contacting a phenolic compound feedstock comprising a phenol having an unsubstituted ortho position selected from phenols and polycyclic phenols having no substituents other than alkyl, hydroxy, aryl, aralkyl and alkaryl in the vapor phase in combination with water vapor at a temperature of 300° to 700° C at a gas hourly space velocity of from 1 $hr^{-1}$ to 2,000 $hr^{-1}$ with a catalyst essentially composed of a member of the class of ceria and combinations of ceria with an oxide of a metal of the group consisting of aluminum, silicon, titanium, zirconium, hafnium, magnesium, calcium, potassium, sodium, lanthanum, neodymium, praseodymium, samarium, thorium, and uranium and mixtures thereof.

2. Process for the production of dibenzofuran which comprises contacting phenol in the vapor phase in combination with water vapor at a temperature of 300° C to 700° C at a gas hourly space velocity of from 1 $hr^{-1}$ to 2,000 $hr^{-1}$ over a catalyst essentially composed of a member of the class of ceria per se, and combinations of ceria with an oxide of a metal of the group consisting of aluminum, silicon, magnesium, titanium, zirconium, hafnium, calcium, potassium, sodium, lanthanum, neodymium, praseodymium, samarium, thorium, and uranium and mixtures thereof.

3. Process as in claim 1 in which the water vapor is present in the proportion of from 0.01 to equal proportion by weight to the phenolic compound feedstock.

4. Process as in claim 2 in which the water vapor is present in the proportion of from 0.01 to equal proportion by weight to the phenol.

5. Process as in claim 2 in which the catalyst is ceria.

6. Process as in claim 5 in which the ceria is dispersed on an alumina carrier.

7. Process as in claim 5 in which the ceria is dispersed on a silica-alumina carrier.

8. Process as in claim 5 in which the ceria is in combination with potassium oxide.

9. Process as in claim 5 in which the ceria is in combination with thorium oxide.

10. Process as in claim 1 in which the feedstock is orthophenylphenol, and the product is a diphenyl derivative of dibenzofuran.

11. Process as in claim 1 in which the feedstock is resorcinol, and the products are 1,7-dihydroxydibenzofuran and 3,7-dihydroxydibenzofuran.

12. Process as in claim 1 in which the feedstock is 1-naphthol, and the product is dinaphthofuran.

13. Process as in claim 1 in which the feedstock is paracresol, and the product is 2,8-dimethyldibenzofuran.

14. Process as in claim 1 in which hydrogen is added to the reaction mixture.

15. Process as in claim 1 in which the catalyst is periodically regenerated by passing an oxygen containing gas over the catalyst at a temperature of from 300° C to 1000° C.

* * * * *